United States Patent
Gerold

(10) Patent No.: US 11,253,731 B2
(45) Date of Patent: Feb. 22, 2022

(54) DEVICES FOR THERAPEUTIC TREATMENT, METHOD OF OPERATING A DEVICE FOR THERAPEUTIC TREATMENT, AND A COMPUTER PROGRAM PRODUCT

(71) Applicant: THERACLION SA, Malakoff (FR)

(72) Inventor: Bjoern Gerold, Paris (FR)

(73) Assignee: Theraclion SA, Malakoff (FR)

( * ) Notice: Subject to any disclaimer, the term of this patent is extended or adjusted under 35 U.S.C. 154(b) by 831 days.

(21) Appl. No.: 16/003,322

(22) Filed: Jun. 8, 2018

(65) Prior Publication Data

US 2018/0353779 A1   Dec. 13, 2018

(30) Foreign Application Priority Data

Jun. 9, 2017   (EP) .................................... 17305694

(51) Int. Cl.
| A61N 7/02 | (2006.01) |
| A61B 8/00 | (2006.01) |
| A61B 90/00 | (2016.01) |
| A61B 18/00 | (2006.01) |

(52) U.S. Cl.
CPC .................. A61N 7/02 (2013.01); A61B 8/54 (2013.01); *A61B 2018/00678* (2013.01); *A61B 2090/0472* (2016.02)

(58) Field of Classification Search
CPC .. A61B 2018/00678; A61B 2090/0472; A61B 8/54; A61N 7/02
See application file for complete search history.

(56) References Cited

U.S. PATENT DOCUMENTS

| 2010/0056924 A1 | 3/2010 | Powers |
| 2010/0106019 A1 | 4/2010 | Friemel et al. |
| 2012/0171169 A1 | 10/2012 | Coussios et al. |

(Continued)

FOREIGN PATENT DOCUMENTS

| EP | 3165167 A1 | 5/2017 |
| WO | 01/66189 A1 | 9/2001 |
| WO | 2010/103469 A1 | 9/2010 |

OTHER PUBLICATIONS

European Search Report Corresponding to 17305694.6 dated Nov. 24, 2017.

*Primary Examiner* — Amelie R Davis
(74) *Attorney, Agent, or Firm* — Finch & Maloney, PLLC; Michael Bujold; Jay Franklin

(57) ABSTRACT

A device (1) for therapeutic treatment of a target (2) comprising at least one ultrasound transducer (3) for generating and transmitting ultrasound pulses to the target and at least one detector (4) to detect ultrasound waves (6) backscattered from structures. The device (1) comprises a signal processing unit (8) to select an output of the at least one detector (4) caused by backscattered waves (6). The selected output has a frequency around an even harmonics of the emitted frequency (f) of the ultrasound pulses. The device (1) comprises a processor (7) to provide an output of the selected signal indicative of a parameter of the backscattered waves (6) in the frequency band around the even harmonics. The processor calculates if the parameter of the backscattered waves (6) in the frequency band is above a preset threshold (13), and provides an alert signal (9) when the parameter exceeds the threshold (13).

16 Claims, 5 Drawing Sheets

(56) References Cited

U.S. PATENT DOCUMENTS

Figure 1:
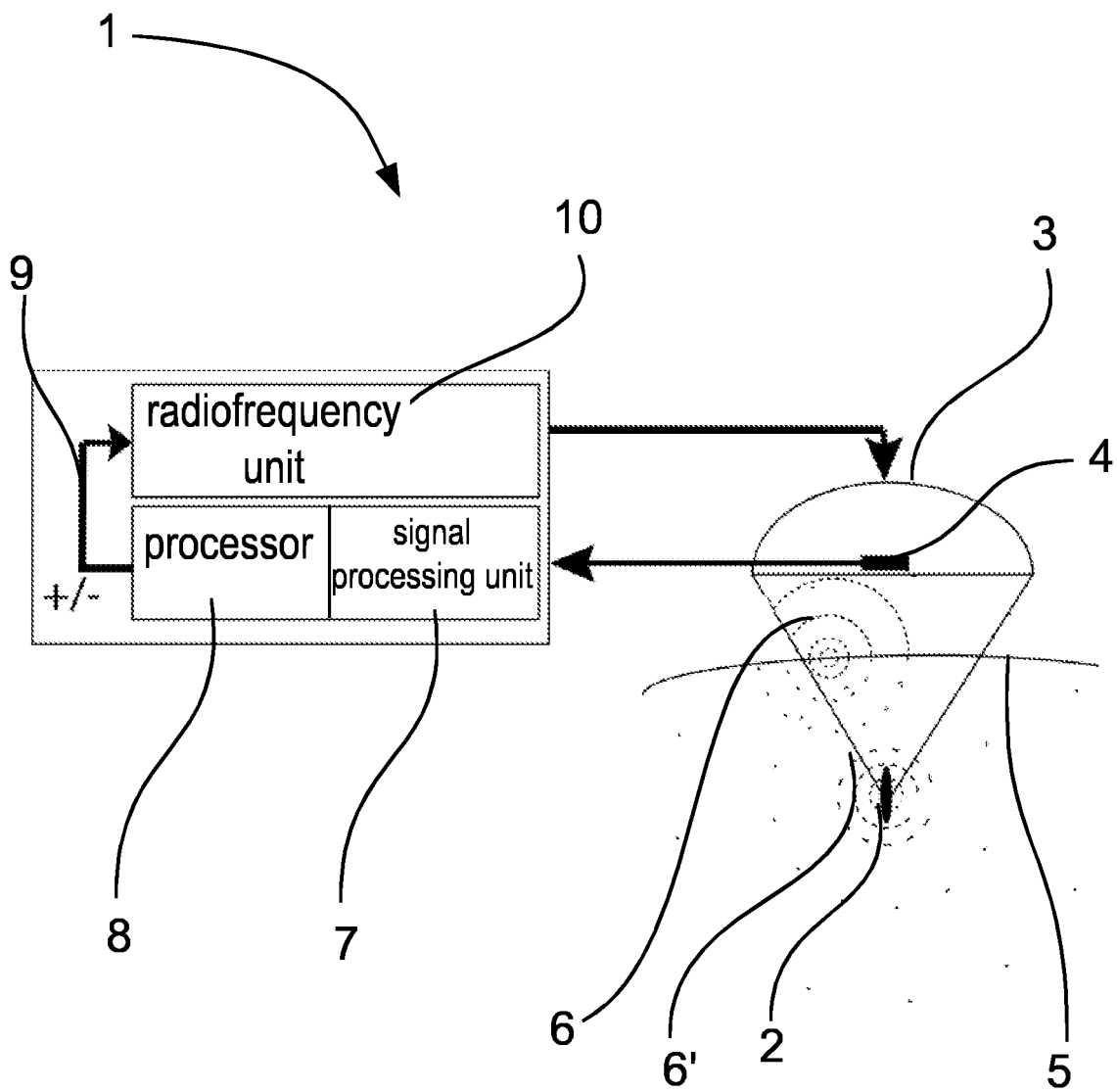

2013/0331685 A1* 12/2013 Liu .................... A61B 5/0042
600/411
2013/0345565 A1 12/2013 Fan et al.
2015/0065871 A1* 3/2015 Konofagou .......... A61B 8/4281
600/431

* cited by examiner

DEVICES FOR THERAPEUTIC TREATMENT, METHOD OF OPERATING A DEVICE FOR THERAPEUTIC TREATMENT, AND A COMPUTER PROGRAM PRODUCT

The present invention is directed to devices tor therapeutic treatment, a method of operating devices tor therapeutic treatment, and a computer program product as defined in the independent claims.

In particular, the invention concerns devices and methods for treatment with ultrasound, especially high intensity focused ultrasounds (HIFU).

Conventionally, in ultrasound treatment, an acoustic treatment transducer emits concentrated acoustic waves onto a target tissue. These waves are absorbed by the tissue, which provokes a temperature rise in the tissue in the target. This temperature elevation in turn induces a local necrosis and thereby allows destruction of living tissue at a distance without any direct contact.

For an optimum efficiency, the ultrasound beam should reach the target unhindered by areas of extreme changes of acoustic impedance.

Such areas of extreme changes of acoustic impedance are commonly present in the form of air bubbles acting as scatters and reflectors of the ultrasound energy. Recent studies have demonstrated that the presence of air bubbles can lead to substantially higher rates of tissue heating, which can be as much as six times the rate of heating in the absence of bubbles [C, C. Coussious, et. al, "Role of acoustic cavitation in the delivery and monitoring of cancer treatment by high-intensity focused ultrasound (HIFU)", Int. J Hyerth., vol., 23, no. 2, ppp. 105-120, 2007)]. Air bubbles can, for example, be present in an acoustic coupling medium or trapped at interfaces, e.g. between the patient's skin and the coupling device. Further, interfaces can present microscopic imperfections leading to unpredictable events such as skin burns.

The skin itself is a hurdle for the transfer of ultrasound energy to a target tissue within the patient. Firstly, the skin presents a change of acoustic impedance along the ultrasonic transmission path, having the effect that a portion of the ultrasound beam is reflected. Secondly, the skin has a relatively high absorption coefficient such that a portion of the ultrasound beam is absorbed. Furthermore, the skin can present inhomogeneous areas such as hairs, scars or dermatologic disorders (e.g. furuncles). Such inhomogeneous areas can act as a nucleation point for bubble formation or can have locally a higher acoustic absorption coefficient, resulting in lower treatment efficiency and skin burns.

With current systems, major skin injuries are not prevented interactively but predictive safety criteria are generally used. These criteria are based on predefined values of delivered maximal and average acoustic intensities at the skin level. These methods assume, however, that the acoustic coupling is optimal (i.e. absence of hairs, scars, dermatologic disorders) or average (i.e. without unusual presence of skin defects or material), see e.g. Ritchie, R., Collin, J., Wu, F., Coussios, C., Leslie, T., & Cranston, D. (2012). *"Significant skin burns may occur with the use of a water balloon in HIFU treatment"* (pp. 289-293), presented at the 11TH INTERNATIONAL SYMPOSIUM ON THERAPEUTIC ULTRASOUND, AIP. http://doi.org/10.1063/1.4757350

Hence, if the acoustic coupling is sub-optimal, e.g. because of any of the above-mentioned reasons, excessive energy might be accumulated at the skin level. The accumulated energy leads to temperature increase and/or the production of bubbles. These can in turn result in unpredicated skin burns and damage of the patient's skin. A further drawback of the presets systems is, that if intensity modulated pulses are used, a predictive technique is difficult to apply because of the stochastic nature of the physical effects (e.g. bubble formation) and the unpredictable skin anatomy.

Hence, there is a need for devices and methods, which overcome the drawbacks of the prior art, in particular for devices and methods which allow an interactive prevention of injuries of intermediate structures caused by ultrasound interaction during ultrasound treatment.

The problem is solved with a device according to the independent claims. In particular, the problem is solved with a device for therapeutic treatment of a target, in particular an organ or tissue. The device comprises at least one ultrasound transducer, in particular a HIFU transducer, for generating and transmitting ultrasound pulses with a frequency ($f$) to said target. The device further comprises at lease one detector adapted to detect ultrasound waves backscattered from structures between said at least one transducer and said target, in particular a skin. Further, the device comprises a signal processing unit adapted to select at least one frequency range of the output of the at least one detector caused by backscattered waves. The selected output has a frequency within a frequency band around an even harmonics of said emitted frequency ($f$) of said ultrasound pulses, preferably around the second harmonics ($2f$). The device further comprises a processor adapted to provide an output of the selected signal indicative of a parameter of the backscattered waves in said frequency band around the even harmonics. In particular, the parameter is an energy of the backscattered waves in said narrow band around the even harmonics. The processor is further adapted to calculate if the parameter of the backscattered waves in the frequency band is above a preset threshold. The processor is also adapted to provide an alert signal in case said parameter is above said threshold.

It has been found that the amount of backscattered waves having an even harmonic frequency, in particular a second harmonics frequency, rapidly increases, when damage of an intermediate structure such as the skin is starting to occur. It has been further observed that the backscattered signal remains at high levels and is therefore indicative of damage.

Such even harmonics can generally only originate from non-linearities but not from the source itself. The ultrasound source does not emit even harmonics itself but might emit odd harmonics ($3f$, $5f$ etc.) because of intrinsic properties of the piezo element in the ultrasound transducer. Hence, the increase in the amount of such backscattered waves is a clear indication that non-linearities, e.g. because of bubble formation at the skin level, occurs.

It has further been observed that detected ultrasound waves backscattered from inside the tissue predominantly have a frequency in a subharmonic broadband whereas detected ultrasound waves backscattered from tissue interfaces are characterized by a signal in the even harmonics band. This is because signals produced inside the tissue with a frequency above $f$ are more readily absorbed by the tissue itself as the absorption coefficient of the tissue is roughly proportional to the acoustic frequency. Therefore, backscattered ultrasound waves originating from the skin level reach the detector with much higher amplitudes than backscattered waves with the same frequency originating from inside the tissue.

At the skin surface, the non-linearities in the ultrasound beam are minimal compared to the ones in the target area. This is because the acoustic propagation is not shocked outside the focus. Hence, detected even harmonics are a strong indication of an unwanted effect such as heating or cavitation (bubble formation) taking place at the skin level. A device according to the invention is therefore especially suitable to detect potential skin damage.

With a device according to the invention, the backscattered signal is detected with a detector. The detector is preferably a passive detector. The output of the detector is then fed into a signal processing unit. The signal processing unit selects the output in a frequency band around an even harmonics. Selection of the output might be performed by digitally and/or analogically filtering the output signal of the detector.

A processor provides an output of the selected signal, which is indicative of a parameter of the backscattered waves in the frequency band. It is especially preferred to indicate the energy of the backscattered waves because the amount of energy absorbed by the structure generally defines the risk of damage.

The processor also calculates if the indicated parameter is above a preset threshold. The threshold is preferably determined empirically as a maximal pressure amplitude or acoustic energy. A rise of the parameter above the threshold is indicative of a risk of damage of the structure (e.g. skin damage). If the parameter is above the threshold, the processor will therefore provide an alert signal.

The alert signal can be provided in various forms. The alert signal might be fed into an electronic system that automatically stops the emission provided such as e.g. an electric signal in a closed feedback loop as described hereinafter. Alternatively, the alert signal might be provided in the form of a visual or acoustic signal which indicates to the user of the device that the parameter is above the threshold. The user might then, for example, adjust or (temporarily) stop ultrasound emission to avoid a damage of the structure.

A device according to the invention therefore interactively informs of or reduce the risk of injuries during ultrasound treatment. Therewith, damage of intermediate structure can be interactively prevented or at least reduced. There is no need for predictive safe criteria which do not allow a distinction on a case by case basis.

Preferably, the frequency band around the even harmonics has a bandwidth depending from the actual systems used.

The bandwidth results from the technical implementation of the filters, the sampling rate of the signal and the HIFU frequency (f) and the processed signal refresh rate and can be typically 100 kHz to 1 kHz. For example with a 1 MHz HIFU frequency, a desired sampling rate to obtain an aliasing-free 2f digitized signal is 5*f, i.e. 5 MHz. Generally 1024 samples are sufficient to calculate the frequency content of the signal in each processed signal data point. This in turn yields a processed signal refresh rate of 200 microseconds, which is equivalent to a frequency resolution of 5 kHz. In the frequency domain, 5 samples around 2f are selected to be certain that the 2f signal is inside the filter output. This translates into a bandwidth of +/−5*5 kHz=+/−25 kHz. The bandwidth ($\Delta_{fil}$) can be calculated with the following formula:

$$\Delta_{fil} = S \times (f_{sampl}/N_{fft\_sampl}).$$

where $f_{sampl}$ is > the Nyquist sampling rate of f and $N_{fft\_sampl}$ is the number of samples required for a discrete Fourier transform.

A processed signal refresh rate of 200 microseconds allows for a minimum delay of the alert signal at 2*200 microseconds which allows for a quick reaction of the system in case a 2f signal is detected. A longer delay can be chosen, with more samples in the processed signal, resulting in a higher resolution in the frequency domain, making possible the selection of a narrower bandwidth, for example 1 kHz.

Typically, the range can be +/−25 kHz, it being understood that the frequency from 25 kHz below the even harmonics up to 25 kHz above the even harmonics is selected. Such a relatively narrow band has been shown to provide reliable results. It is narrow enough to selectively indicate the relevant backscattered signal but broad enough to allow the recognition of the backscattered signal with the relevant frequency.

In an illustrative example, the transducer is a HIFU transducer adapted to emit HIFU waves with a frequency (f) of 1 MHz. The backscattered signal is filtered around the second harmonics (2f), i.e. 2 MHz with a bandwidth of 50 kHz, i.e. +/−25 kHz. Such a setup has shown to reliably indicate the start and presence of skin damage.

The at least one ultrasound transducer is preferably adapted to receive the alert signal of the processor and further adapted to temporarily or definitely stop emission of ultrasound as a result of the received alert signal.

Such a closed feedback loop allows a direct control of the at least one ultrasound transducer based on the calculated parameter of the selected bandwidth.

The ultrasound transducer generally comprises a radiofrequency unit, which powers the acoustic transducer. The alert signal is preferably received by the radiofrequency unit which then temporarily or definitely stops emission of ultrasound waves of the ultrasound transducer.

In an especially preferred feedback loop, the ultrasound transducer is temporarily shut down when the parameter reaches the threshold to protect the intermediate structure. It has been observed that the parameter of the selected even harmonics signal drops immediately after emission of ultrasound has been reduced or stopped. When the parameter has dropped, ultrasound emission will be resumed until the parameter reaches the threshold again resulting again in a temporary throttling of the ultrasound transducer.

Preferably, the ultrasound transducer is adapted to definitely stop ultrasound emission after a predefined number of temporary throttlings has been reached, e.g. after $N_{max}$ temporary throttlings. $N_{max}$ can be related to a maximum allowable energy received by the detector in the bandwidth around 2f. $N_{max}$ can be estimated as:

$$N_{max} = E_{max}/((N_{fft\_sampl}/f_{sampl}) \times [0.01 \text{ mW/mm}^2 \text{ to } 100 \text{ mW/mm}^2])$$

or preferably $$N_{max} = E_{max}/((N_{fft\_sampl}/f_{sampl}) \times [0.1 \text{ mW/mm}^2 \text{ to } 10 \text{ mW/mm}^2]).$$

where $E_{max} < 1 \text{ J/mm}^2$, which is the maximal detected acoustic energy.

Therewith, an accumulation of energy in the intermediate structure can even better be prevented as tissue will not be heated over (too) long period.

Preferably, the signal processing unit is further adapted to select the output of the at least one detector caused by the backscattered waves in subharmonic ranges lower than said emitted frequency (f) of said ultrasound pulses.

Preferably, the processor is adapted to provide an output of the selected signal indicative of a parameter of the backscattered waves in said subharmonic frequency, in particular an energy of the backscattered waves in said subharmonic frequency.

As described hereinabove, it has been observed that ultrasound waves backscattered from inside the tissue have mainly a frequency in the subharmonics range. If has further been observed that backscattering in the subharmonic band is an indicator of successful treatment parameters such as boiling or cavitation activity. By selecting also the subharmonic ranges, the device can be used to monitor e.g. cavitation events that occur in the target area.

Further, the subharmonic broadband signal can be used to help setting the threshold.

Preferably the signal processing unit is further adapted to select the output of the at least one detector caused by the backscattered waves having a frequency within a frequency band around a half harmonics (f/2) of said emitted frequency (f).

The half harmonics provide a useful indication of successful treatment within the subharmonics band. Therefore, by selecting in the half harmonics, cavitation or boiling events occurring in the target area can reliably be monitored.

The threshold for the even harmonics should preferably in a range of acoustic power 0.01 mW/mm2 to 100 mW/mm2 or preferably 0.1 mW/mm2 to 10 mW/mm2 on the detector surface. In addition or alternatively the energy emitted at skin level should be preferably not more than $E_{s\_max}$, in order to avoid skin damage. It is also advantageous to subtract from the 2f signal the acoustic power of the sub harmonic signal to achieve a better reading, eliminating the signals originating from wanted bubble activity at the focus.

Preferably, the signal processing unit is further adapted to select the output of the at least one detector caused by the backscattered waves in a second frequency range B2, other than the even harmonics bandwidth B1 as defined above. Thereby a reference signal can be generated. Preferably B2 is close to B1 but does not overlap with B1. Preferably the width of B2 is equal to the width of B1. For example B2 is 1.8*f +/−25 khz.

Preferably, the processor is adapted to provide an output of the selected signal indicative of a parameter of the backscattered waves in said B2, in particular an energy of the backscattered waves in said B2.

Further, the reference signal can be used to help correcting the B1 signal. For example the B2 signal may be subtracted from the B1 signal to yield a corrected B1 signal where the variations due to ultrasonic activity outside the skin level are eliminated or attenuated.

The invention further concerns a method of operating a device for therapeutic treatment of a target, preferably a device as described hereinbefore. The method comprises she steps of:
  generating and emitting ultrasound pulses with a frequency (f) with at least one ultrasound transducer, in particular a HIFU transducer
  detecting backscattered ultrasound waves with at least one detector, backscattered from structures between said at least one transducer and said target,
  selecting at least one frequency range of an output of the at least one detector caused by backscattered waves within a frequency band around an even harmonics of said emitted frequency (f) of said ultrasound pulses, preferably around the second harmonics (2f), with a signal processing unit,
  providing an output of the analyzed signal indicative of a parameter of the backscattered waves in said frequency band around the even harmonics, in particular an energy of the backscattered waves in said frequency band, with a processor,
  calculating with said processor if the parameter of the backscattered waves in said frequency band is above a preset threshold and
  providing an alert signal in case said parameter is above said threshold.

Preferably, the frequency band around the even harmonics has a bandwidth of 50 kHz, i.e. +/−25 kHz.

Preferably, the alert signal is received by the at least one ultrasound transducer and emission of ultrasound waves is temporarily or definitely stopped or reduced.

The method preferably comprises the further step of selecting the output of the at least one detector caused by the backscattered waves in subharmonic ranges lower than the emitted frequency (f), preferably with a filter.

Preferably, an output of a parameter of the selected signal in the subharmonic range is provided with the processor.

Preferably, the output of the at least one detector caused by the backscattered waves having a frequency within a frequency band around a half harmonics (f/2) of said emitted frequency (f) is selected.

The invention is further directed to a method of treating tissue with an ultrasound beam from a therapeutic treatment transducer, preferably a device as described hereinbefore. The method comprises the steps of:
  generating and emitting ultrasound pulses with a frequency (f) with at least one ultrasound transducer, in particular a HIFU transducer
  detecting backscattered ultrasound waves with at least one detector, backscattered from structures between said at least one transducer and said target,
  selecting at least one frequency range of an output of the at least one detector caused by backscattered waves within a frequency band around an even harmonics of said emitted frequency (f) of said ultrasound pulses, preferably around the second harmonics (2f) with a signal processing unit,
  providing an output of the selected signal indicative of a parameter of the backscattered waves in said frequency band around the even harmonics, in particular an energy of the backscattered waves in said frequency band, with a processor,
  calculating with said processor if the parameter of the backscattered waves in said frequency band is above a preset threshold and
  providing an alert signal in case said parameter is above said threshold.

Preferably, the frequency band around the even harmonics has a bandwidth of 100 kHz to 1 kHz.

Preferably, the alert signal is received by the at least one ultrasound transducer and emission of ultrasound waves is temporarily or definitely stopped or reduced.

The method preferably comprises the further step of selecting the output of the at least one detector caused by the backscattered waves in subharmonic ranges lower than the emitted frequency (f), preferably with a filter.

Preferably, an output of a parameter of the selected signal in the subharmonic range is provided with the processor Preferably, the output of the at least one detector caused by the backscattered waves having a frequency within a frequency band around a half harmonics (f/2) of said emitted frequency (f) is selected.

It has further been found that backscattered signals, in particular outside the emission frequency band, are often linked to tissue effects. Tissue effects include voluntary, i.e. therapeutic effects and non-voluntary, i.e. adverse events such as skin burn effects.

Therefore, it is desirable to have a device which is adapted to not only analyze the signal during ultrasound exposure but also to localize where in the tissue the phenomena occur.

The problem is solved with a further device according to the further independent claim. The problem is solved in particular with a device for therapeutic treatment of a target, in particular an organ or tissue, preferably a device as described hereinabove. The device comprises at least one ultrasound transducer, in particular a HIFU transducer, for generating and transmitting ultrasound pulses with a frequency (f) to said target. The device further comprises at least one detector adapted to detect ultrasound waves backscattered from structures between said at least one transducer and said target, in particular a skin. Further, the device comprises a signal processing unit adapted to select at least one frequency range of an output of the at least one detector caused by backscattered waves having a frequency within a frequency band around an even harmonics of said emitted frequency (f) of said ultrasound pulses, preferably around the second, harmonics (2f). A processor of the device is adapted to provide an output of the selected signal indicative of a parameter of the backscattered waves in said frequency band around the even harmonics, in particular an energy of the backscattered waves in said narrow band around the even harmonics. The signal processing unit is further adapted to select a frequency range of the output of the at least one detector caused by the backscattered waves in subharmonic ranges lower than said emitted frequency (f) of said ultrasound pulses. The processor is further adapted to provide an output of the selected signal indicative of a parameter of the backscattered waves in said subharmonic frequency. The processor is further adapted to monitor the outputs in the even harmonic and the subharmonic range in parallel. In particular the processor may be adapted provide the outputs as a plot against time.

As described hereinbefore, ultrasound waves backscattered from bubbles formed inside the tissue predominantly can be detected by a frequency in a subharmonic broadband. Ultrasound waves backscattered from tissue interfaces are characterized by a signal in the even harmonics band.

Further, it has been observed that when the variance of subharmonic broadband signal increases, the variance of the even harmonic signal also increases due to the broadband nature of such emission. However, the even harmonics signal is frequency-specific and does not have a contribution to the selected subharmonics signal.

Hence, if the signal contains a predominant frequency component around the even harmonics, it is known that the backscattered waves originate from the tissue/balloon interface. The method therefore allows identifying if the signal originates from an interface such as skin and differentiates it from acoustic signals from inside the tissue. The backscatter signal can either originate from the target area at the ultrasound focus or at the skin or somewhere in between.

If the signal originates from skin/balloon interface experiments have shown that a strong even harmonic component is produced as a result of skin damage. It also has been observed that in this case only minimal sub harmonic emission is detected.

In the case of bubble formation at the target, both sub harmonic and even harmonic and also general broadband noise can be produced. When sub harmonic emissions are detect they are detected more readily than higher frequency components. This is due to the fact that tissue absorbs more efficiently higher frequency signals. Naturally may occur a combination of the two cases above. Therefore the threshold has to be set above the even harmonic signal originating from the target, but below a limit determined to be dangerous if it solely occurs at the skin (determined experimentally in advance).

The processor is preferably further adapted to calculate if the parameter of the backscattered waves in the frequency band is above a preset threshold and wherein the processor is adapted to provide an alert signal in case said parameter is above said threshold.

Preferably, the frequency band around the even harmonics has a bandwidth of 100 kHz to 1 kHz.

Preferably the alert signal is received by the at least one ultrasound transducer and emission of ultrasound waves is temporarily or definitely reduced.

The invention further concerns a computer program product comprising software code portions adapted to perform the steps of a method as described hereinbefore, when the program is run on a computer.

The computer to run the program is preferably a processor integrated in a device as described hereinbefore.

The invention further concerns a method to identify the origin of a relevant signal during ultrasound treatment with a therapeutic treatment transducer, preferably a device as described hereinbefore. The method comprises the steps of:

generating and emitting ultrasound pulses wish a frequency (f) with at least one ultrasound transducer, in particular a HIFU transducer detecting backscattered ultrasound waves with at least one detector, backscattered from structures between said at least one transducer and said target, selecting at least one frequency range of an output of the at least one detector caused by backscattered waves within a frequency band around an even harmonics of said emitted frequency (f) of said ultrasound pulses, preferably around the second harmonics (2f) with a signal processing unit, providing an output of the selected signal indicative of a parameter of the backscattered waves in said frequency band around the even harmonics, in particular an energy of the backscattered waves in said frequency band, with a processor, selecting a frequency range of the output of the at least one detector caused by the backscattered waves in subharmonic ranges lower than the emitted frequency (f), preferably with a filter providing an output of the selected signal indicative of a parameter of the backscattered waves in said subharmonic frequency, wherein both outputs of the processor are monitored in parallel, in particular plotted against time.

Preferably, it is calculated if the parameter of the backscattered waves in the frequency band is above a preset threshold and wherein the processor is adapted to provide an alert signal in case said parameter is above said threshold wish the processor.

Preferably, the frequency band around the even harmonics has a bandwidth of 100 kHz to 1 kHz.

Preferably, the at least one ultrasound transducer is adapted to receive the alert signal of the processor and wherein the at least one ultrasound transducer is adapted to temporarily or definitely stop ultrasound emission as a result of the received alert signal.

While the various steps of selecting and determining have been described with reference to a one signal processing unit and one single processor it is understood that several selecting or calculating tasks might be carried out on separate units and/or processors, which still is encompassed by the present claims.

Figure 2:
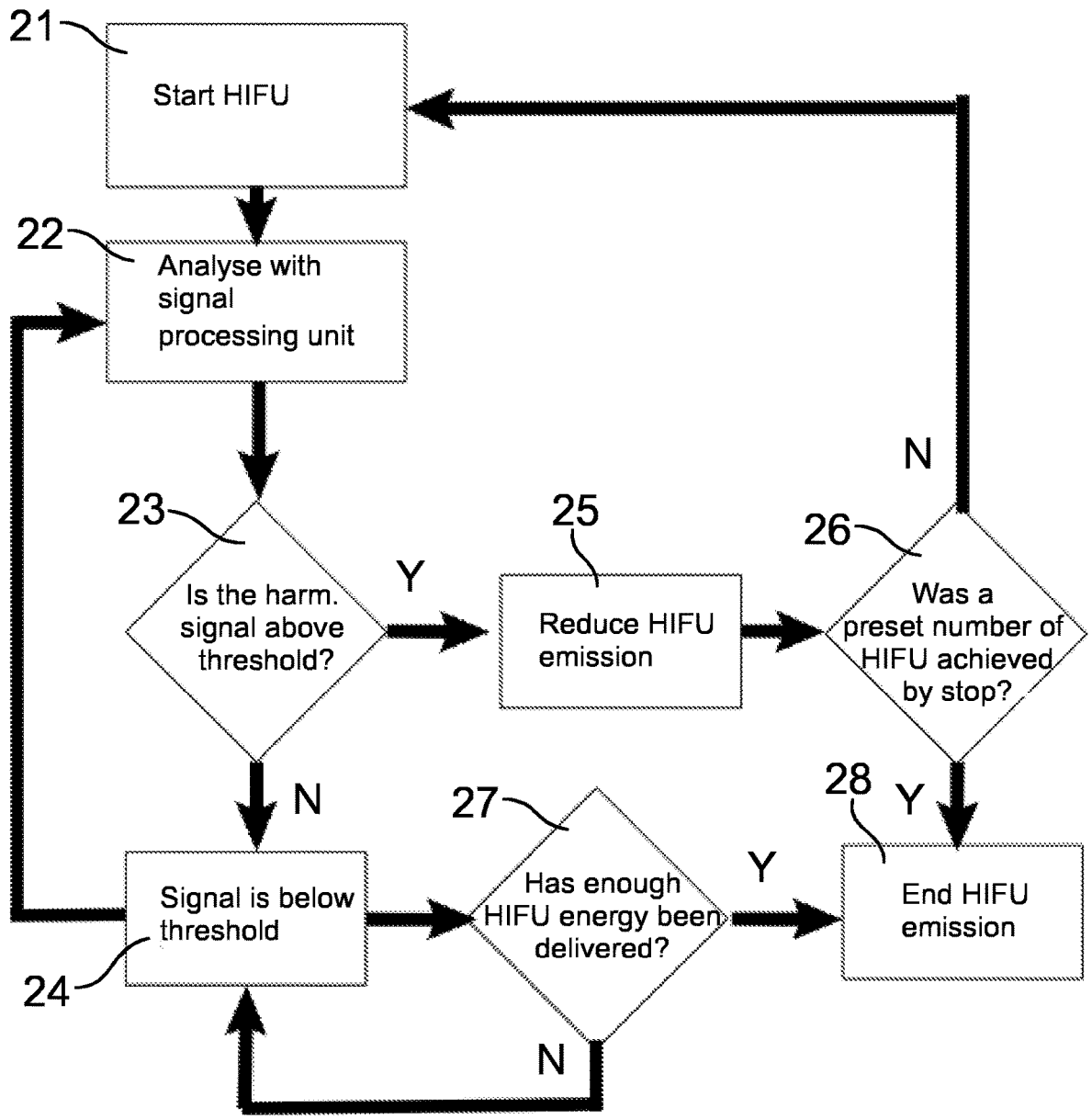
Figure 3:
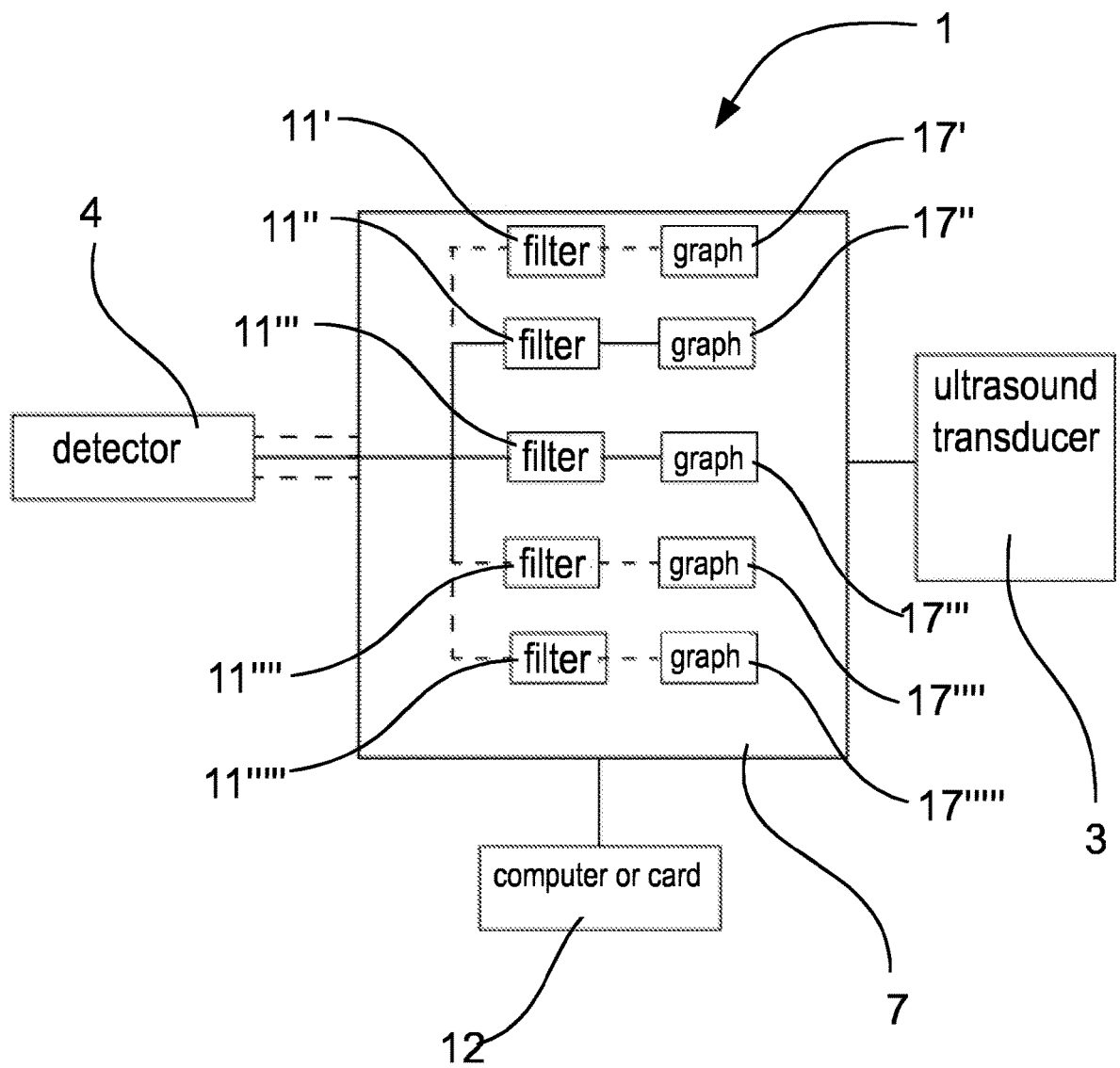
Figure 4A:
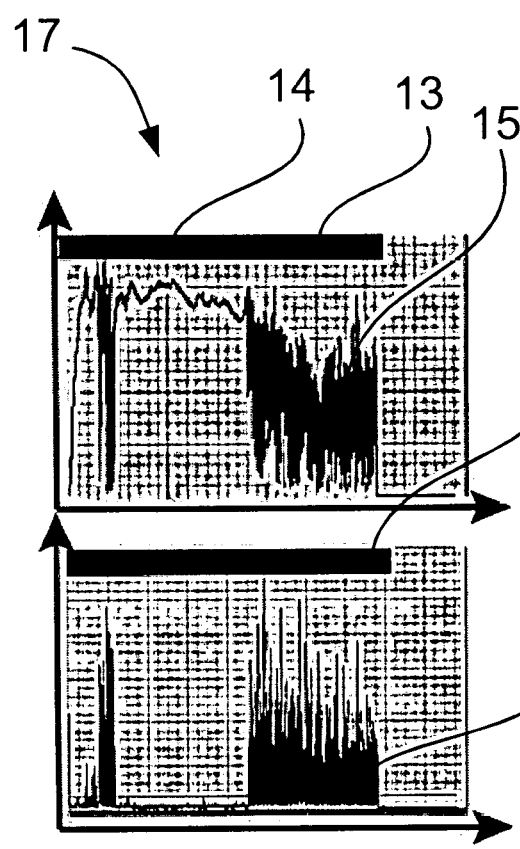

Further aspects of the invention are described with reference to the figures. The figures schematically show:

FIG. 1: A device according to the invention;

FIG. 2: a flow chart of a concept according to the invention;

FIG. 3: a schematic representation of a device according to the invention;

FIG. 4a/b: graphs indicating outputs of the processor.

Figure 5:
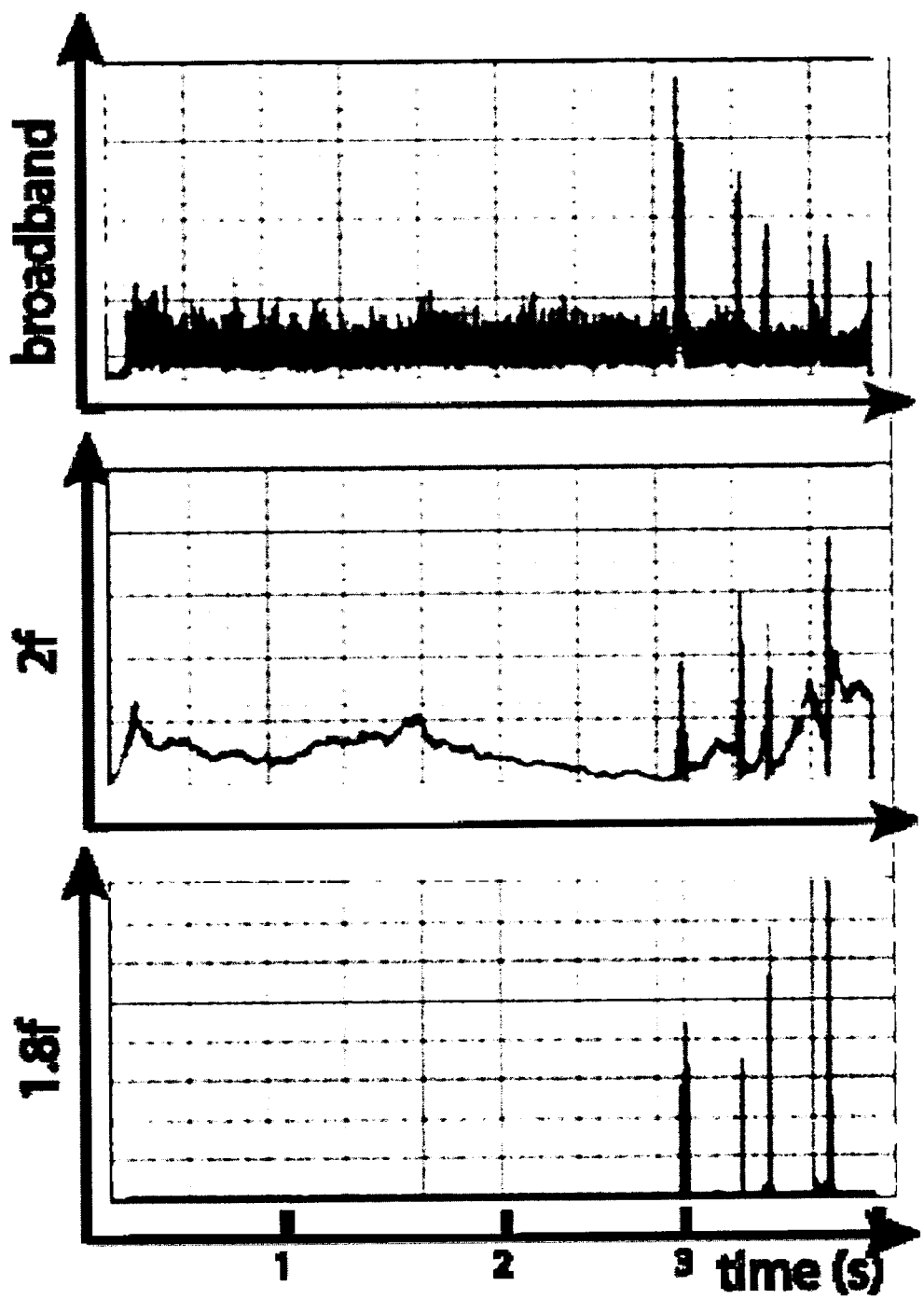

FIG. 5: graphs indicating several simultaneous outputs of the processor according to a further embodiment of the invention.

FIG. 1 schematically shows a device 1 according to the present invention. The device 1 comprises an ultrasound transducer 3 in the form of a HIFU transducer. The ultrasound transducer 3 is powered by a radiofrequency unit 10 at a frequency f of e.g. 1 MHz. The ultrasound pulses with the frequency f are focused on the target 2. On their way to the target if the high intensity focused ultrasound waves travel through the skin 5 of the patient. A portion of the emitted ultrasound waves are backscattered at the boundary of the skin. The backscattered waves 6 are detected by a detector 4.

The backscattered waves 6 as compared to the emitted waves can arise from non-linearities in the propagation path. Such non-linearities are minimal at the skin 5 surface compared to the ones in the target area 2 because the acoustic intensities are much lower. However, when unwanted effects arise at the skin level, the non-linearities increase which can be detected via the backscattered waves 6. Detected backscattered waves 6 originating from the skin level 5 have a much higher amplitude in the second harmonics (and other even harmonics) than detected backscattered waves 6' originating from inside the tissue. Backscattered waves 6' with a frequency larger than f are mostly absorbed by the surrounding tissue.

The detector 4 will provide an output signal of the detected backscattered waves 6 and 6' to a signal processing unit 7. The signal processing unit 7 will select a frequency range B1 around the second harmonics 2f from the output signal of the detector 4 with a narrow passband filter 11" (see FIG. 3). A processor 8 will then provide an output of the filtered signal indicating the energy of the backscattered waves 6 in the second harmonics (see FIG. 4b). The processor 8 calculates if the energy of these waves is above a certain threshold 13 (see FIG. 4b). If the energy of the backscattered waves 6 in the even harmonics exceeds the threshold 13, the processor provides an alert signal 9. The radiofrequency unit 10 of the ultrasound transducer 3 will receive the alert signal 9 and will interrupt the emission of HIFU waves by the ultrasound transducer 3.

FIG. 2 shows an exemplary flowchart of the functionality of the present invention. Processes are shown as rectangles, decisions are shown as diamonds and the flow lines as arrows. If a decision is positively made it is indicated with a Y, negatively taken decisions are indicated with N. Rectangle 21 indicates the starting of HIFU with the ultrasound transducer 3 (see FIG. 1). Upon the start of HIFU, an even harmonic signal of backscattered waves (see FIG. 1) is detected by the detector 4 (see FIG. 1) and analyzed with the signal processing unit 7 (see FIG. 1), indicated by rectangle 22. The detection of even harmonics leads to a decision if the detected even harmonic signal is above a threshold 13 (see FIG. 4b) made by the processor 8 (see FIG. 1), indicated by diamond 23. If the analyzed signal of the backscattered even harmonics waves 6 is below the threshold 13, HIFU is continued (rectangle 24). If the signal is above the threshold, HIFU emission of the transducer 3 is reduced (rectangle 25).

In case the HIFU emission is reduced (rectangle 25), a decision has to be made if a preset number of HIFU stopping has been achieved by the step in rectangle 25, indicated by diamond 26. If the preset number has been achieved, HIFU emission is ended (rectangle 28), if the preset number has not been achieved, HIFU is again started (rectangle 21).

In case emission is continued (rectangle 24), a decision will have to be made if all HIFU energy has been delivered as indicated by diamond 27. If this is not the case, HIFU is continued (rectangle 24). If this is the case, HIFU is ended (rectangle 28). During the continued emission of HIFU (rectangle 24), the backscattered signal is continuously detected and analyzed. If an even harmonics signal is detected during the continued emission (rectangle 22), a decision if the signal is above the threshold 13 has to be made (diamond 23).

FIG. 3 shows an exemplary device 1 according to the invention. In particular, FIG. 3 shows a detailed view of the signal processing unit 7. One or more outputs of the detector 4 are fed into the signal processing unit. The signal processing unit 7 comprises a number of passband filters 11'-11"" (e.g. five) arranged in parallel.

In this embodiment, filter 11' filters in a harmonic nf, filter 11" filters in the second harmonics 2f, filter 11'", filters in a subharmonic range <f, filter 11"" filters in the half harmonics f/2 and filter 11""' in a portion of the frequency f/n, wherein n=1, 2, 3, 4, 5, 6 . . . . Analyzing the signal in different frequency domains allows a better distinction of the origin of the backscattered ultrasound waves 6 and 6'. Ultrasound waves 6' backscattered from inside the tissue (e.g. a hyperechoic mark visible with an on-line US scanner) are predominantly detected in the sub harmonic range and only moderately as even higher harmonics. Backscattered waves 6 from the skin 5 in the even harmonics will not have an influence of signals in the subharmonics range. Therewith, if only a signal in the even harmonics is detected, but not in the subharmonics, the origin of the backscattered waves is the skin where an unwanted effect occurs.

The filtered signal is processed with a processor 8 (see FIG. 1) providing an output indicating the energy of the backscattered waves 6 (see FIG. 1). The processor 8 also calculates if the energy/acoustic pressure is above a preset threshold 13 (see FIG. 4b). The processor provides an output indicating the energy in the form of graphs 17 (see also FIG. 4b). If the energy of the backscattered waves 6 in the second harmonics is above she threshold 13 indicated in graph 17", the transducer 3 is temporarily shut down or its output reduced.

The whole process is executed on an analogic or digitally implemented electronic card.

Figure 4B:
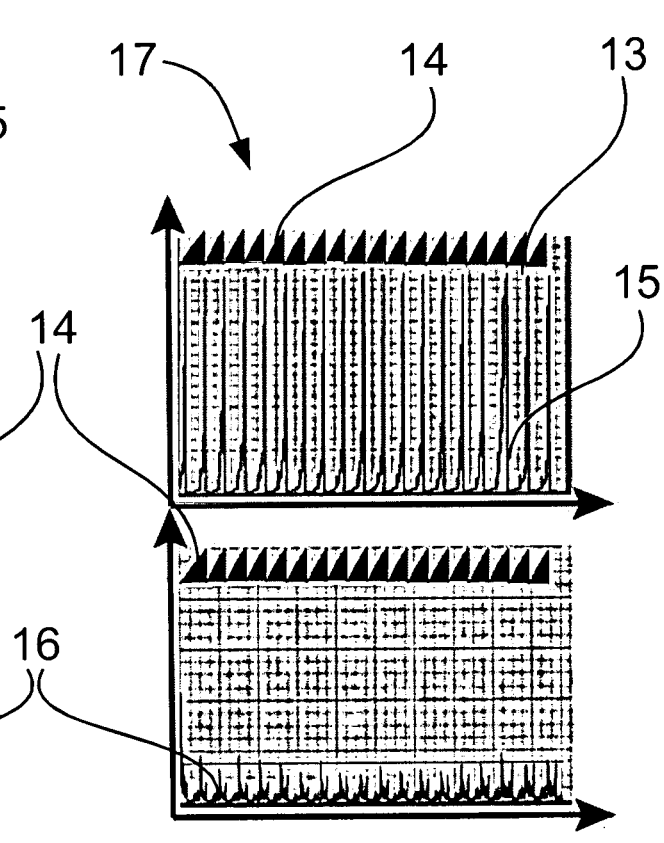

FIGS. 4a and 4b show graphs 17 indicating the output of a processor.

FIG. 4a shows graphs 17 of a processor, where no safety algorithm was run, i.e. were the transducer 3 (see FIG. 1) was not shut down when the energy of the backscattered waves 6 (see FIG. 6) is above a threshold 13. The upper graph displays a signal 15 indicating the energy (y-axis) of the backscattered waves 6 with a second harmonics frequency over time (x-axis). The constant HIFU emission is indicated as a black band 14. The lower graph displays a signal 14 indicating the energy (y-axis) of the backscattered waves 6' in a subharmonic frequency over time (x-axis).

As shown, the even harmonics signal 15 starts simultaneously with the HIFU emission and rapidly increases. In the beginning, the signal 16 in the subharmonic range remains low, being indicative that no wanted effect occurs in the target. In FIG. 4a, the emission is not reduced when the signal 15 of the second harmonics reaches the threshold 13, therefore skin damage will occur. After a while, the subharmonic signal will also increase indicating an effect in the target. Cavitation (bubble formation) is a stochastic phenomenon. Therefore the bubbles can disappear, e.g. by blood flow if the bubble formation occurred inside a blood flow or when the energy at the target decreases because it is intercepted at skin level.

FIG. 4*b* shows graphs 17 with an activated safety algorithm. As in FIG. 4*a*, the upper graph shows the signal around the second harmonics frequency, the lower in a subharmonics frequency. As soon as the energy of the backscattered waves 6 around the second harmonics reach the threshold 13, HIFU emission is reduced. The HIFU emission is shown as black triangles 14 indicating that the emission of HIFU is interrupted over time by the safety algorithm.

FIG. 5 illustrates a further preferred method according to the invention.

FIG. 5 shows, from top to bottom:
1. the subharmonic broadband signal. Spikes appear after 3s and are indicative of bubble activity within the tissue.
2. the signal within a first frequency range B1 around an even harmonic, (50 kKz around 2*f, i.e. 2 MHz)
3. the signal within a second frequency range B2 neighboring but not including an even harmonic (50 kKz around 1.8*f, i.e. 1.8 MHz)

A corrected signal starting from B1 can be generated as follows:

An activity such as spikes in B2 is identified

The spikes are removed from the signal B1 if they appear simultaneously with the ones in B2

A corrected B1 signal is a better representative of possible harmful activity at the skin level.

If the alert signal was triggered by an uncorrected signal B1, the energy to the transducer would have been unnecessarily reduced or stopped at 3s. In contrast, since the spikes have been removed from the initial signal, the treatment was able to proceed without interruption.

The invention claimed is:

1. A device for therapeutic treatment of a target, formed by an organ or tissue, wherein the device comprises:
    at least one high intensity focused ultrasound (HIFU) transducer, for generating and emitting ultrasound pulses with a frequency to said target,
    at least one detector adapted to detect backscattered waves, the backscattered waves being backscattered from structures between said at least one transducer and said target, and to generate a detector-output,
    a signal processing unit adapted to select a first signal of at least one first frequency range of the detector-output, wherein the at least one first frequency range is within a frequency band around an even harmonic of said emitted frequency of said ultrasound pulses,
    a processor adapted to provide a first processor-output based on the selected first signal, wherein the first processor-output is indicative of a first parameter of the backscattered waves in said frequency band around the even harmonic, wherein the processor is further adapted to calculate if the first parameter of the backscattered waves in the frequency band is above a preset first threshold and wherein the processor is adapted to provide a first alert signal in case said first parameter is above said first threshold, wherein the signal processing unit is further adapted to select a second signal of a second frequency range of the detector-output, wherein the second frequency range is in a subharmonic range lower than said emitted frequency of said ultrasound pulses,
    wherein the processor is additionally adapted to provide a second processor-output of the selected second signal, wherein the second processor-output is indicative of a second parameter of the backscattered waves in said subharmonic ranges lower than said emitted frequency, wherein the processor is further adapted to calculate if the second parameter of the backscattered waves in the second frequency range is above a preset second threshold and wherein the processor is adapted to provide a second alert signal in case said second parameter is above said second threshold.

2. The device according to claim 1, wherein the frequency band around the even harmonic is based on at least one of a filter, a sampling rate of the selected first signal, the frequency of the HIFU transducer or a processed signal refresh rate and +/−25 kHz around the frequency of the even harmonic.

3. The device according to claim 1, wherein the at least one HIFU transducer is adapted to receive the first alert signal and/or second alert signal of the processor and the at least one HIFU transducer is adapted to temporarily or permanently reduce ultrasound emission as a result of at least one of the received first alert signal and second alert signal.

4. The device according to claim 1, wherein the second frequency range is within a frequency band around a half harmonic of said emitted frequency.

5. The device according to claim 1,
    wherein the signal processing unit is further adapted to select a third signal of at least one third frequency range of the detector-output, wherein the at least one third frequency range is a third frequency range, other than but neighboring the even harmonic range,
    the signal processing unit is further adapted to identify irregular patterns in a reference signal, generated by the third signal, and
    the signal processing unit is adapted to correct the detector-output on the basis of said irregular patterns, by subtracting said irregular patterns from the detector-output.

6. A method of operating a device for therapeutic treatment of a target, the method comprising the steps of:
    generating and emitting ultrasound pulses with a frequency with at least one high intensity focused ultrasound (HIFU) transducer,
    detecting backscattered waves with at least one detector, wherein the backscattered waves are backscattered from structures between said at least one HIFU transducer and said target,
    generating a detector-output, using the detector,
    selecting at least one first signal of at least one first frequency range of the detector-output, wherein the at least one first frequency range is within a frequency band around an even harmonic of said emitted frequency of said ultrasound pulses using a signal processing unit,
    providing a first processor-output, using a processor, of the selected first signal, wherein the first processor-output is indicative of a first parameter of the backscattered waves in said frequency band around the even harmonic,
    calculating if the first parameter of the backscattered waves in said frequency band is above a preset first threshold, using the processor, and providing a first alert signal in case said first parameter is above said first threshold, selecting a second signal of at least one second frequency range of the detector-output, wherein the at least one second frequency range is in subharmonic ranges lower than the emitted frequency, using the signal processing unit, providing a second processor-output of the selected second signal, wherein the second processor-output is indicative of a second parameter of the backscattered waves in said subharmonic ranges lower than the emitted frequency, using the processor, calculating if the second parameter of the backscattered waves in said at least one second frequency range is above a preset second threshold using the processor and providing a second alert signal in case said second parameter is above said second threshold.

7. The method according to claim 6, wherein the frequency band around the even harmonic has a bandwidth of 100 kHz to 1 kHz.

8. The method according to claim 6, wherein the first alert signal and/or second alert signal is received by the at least one HIFU transducer and emission of ultrasound pulses is temporarily or permanently reduced.

9. A device for therapeutic treatment of a target, wherein the device comprises:
 at least one high intensity focused ultrasound (HIFU) transducer for generating and emitting ultrasound pulses with a frequency to said target,
 at least one detector adapted to detect backscattered waves, the backscattered waves being backscattered from structures between said at least one HIFU transducer and said target, and
 a signal processing unit adapted to select a first signal of at least one first frequency range of a detector-output, wherein the at least one first frequency range is within a frequency band around an even harmonic of said emitted frequency of said ultrasound pulses,
 a processor adapted to provide a first processor-output of the selected first signal, wherein the first processor-output is indicative of a first parameter of the backscattered waves in said frequency band around the even harmonic,
 wherein the signal processing unit is further adapted to select a second signal of an at least one second frequency range of the detector-output, wherein the at least one second frequency range is in subharmonic ranges lower than said emitted frequency of said ultrasound pulses,
 the processor is further adapted to provide a second processor-output of the selected second signal, wherein the second processor-output is indicative of a second parameter of the backscattered waves in said subharmonic ranges, and
 the processor is adapted to monitor said second processor-output indicative of the second parameter and the first processor-output indicative of the first parameter.

10. The device according to claim 9, wherein the processor is further adapted to calculate if the first parameter of the backscattered waves is above a preset first threshold or the second parameter of the backscattered waves is above a preset second threshold and the processor is adapted to provide a first alert signal in case said first parameter is above said first threshold and/or a second alert signal if said second parameter is above said second threshold.

11. The device according to claim 10, wherein the at least one HIFU transducer is adapted to receive the first alert signal and/or second alert signal of the processor and the at least one HIFU transducer is adapted to temporarily or permanently reduce ultrasound emission as a result of the received first alert signal and/or second alert signal.

12. The device according to claim 10, wherein the frequency band around the even harmonic has a bandwidth of 100 kHz to 1 kHz.

13. A non-transitory computer readable medium comprising software code portions adapted to perform the steps of the method according to claim 8, when the program is run on a computer.

14. A method to identify if the origin of a relevant signal during ultrasound treatment with at least one therapeutic treatment high intensity focused ultrasound (HIFU) transducer originates from a target or from structures between the at least one HIFU transducer and the target, comprising the steps of:
 generating and emitting ultrasound pulses with a frequency using the at least one HIFU transducer,
 detecting backscattered waves with at least one detector, backscattered from structures between said at least one HIFU transducer and said target,
 generating a detector-output, using the detector,
 selecting a first signal, using a signal processing unit, of at least one first frequency range of the detector-output, wherein the at least one first frequency range is within a frequency band around an even harmonic of said emitted frequency of said ultrasound pulses,
 providing a first processor-output of the selected first signal, wherein the first processor-output is indicative of a first parameter of the backscattered waves in said frequency band around the even harmonic, using a processor,
 selecting a second signal of at least one second frequency range of the detector-output, wherein the at least one second frequency range is in subharmonic ranges lower than the emitted frequency, and
 providing a second processor-output of the selected second signal, wherein the second processor-output is indicative of a second parameter of the backscattered waves in said subharmonic ranges,
 wherein the first and second processor-output of the processor are monitored in parallel.

15. The method according to claim 14, wherein it is calculated if the first parameter of the backscattered waves is above a preset first threshold or the second parameter of the backscattered waves is above a preset second threshold and the processor is adapted to provide a first alert signal in case said first parameter is above said first threshold and/or a second alert signal if said second parameter is above said second threshold.

16. The method according to claim 14, wherein the frequency band around the even harmonic has a bandwidth of 100 kHz to 1 kHz.

* * * * *